(12) United States Patent
Guo et al.

(10) Patent No.: US 12,721,986 B2
(45) Date of Patent: Sep. 1, 2026

(54) SYSTEMS AND METHODS FOR MICRONEEDLE THERAPEUTIC DELIVERY WITH ACOUSTIC SIGNALS

(71) Applicant: THE TRUSTEES OF INDIANA UNIVERSITY, Bloomington, IN (US)

(72) Inventors: Feng Guo, Bloomington, IN (US); Hongwei Cai, Bloomington, IN (US); Junhua Xu, Chengdu (CN)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 461 days.

(21) Appl. No.: 18/290,105

(22) PCT Filed: May 11, 2022

(86) PCT No.: PCT/US2022/028682
§ 371 (c)(1),
(2) Date: Nov. 9, 2023

(87) PCT Pub. No.: WO2022/240928
PCT Pub. Date: Nov. 17, 2022

(65) Prior Publication Data

US 2025/0332397 A1 Oct. 30, 2025

Related U.S. Application Data

(60) Provisional application No. 63/187,793, filed on May 12, 2021.

(51) Int. Cl.
*A61M 37/00* (2006.01)

(52) U.S. Cl.
CPC .... *A61M 37/0092* (2013.01); *A61M 37/0015* (2013.01); *A61M 2037/0023* (2013.01); *A61M 2037/0061* (2013.01)

(58) Field of Classification Search
CPC .......... A61M 37/0015; A61M 37/0092; A61M 2037/0023; A61M 2037/0061
See application file for complete search history.

(56) References Cited

U.S. PATENT DOCUMENTS

| | | | | |
|---|---|---|---|---|
| 6,620,123 | B1 * | 9/2003 | Mitragotri | A61M 37/0092 604/22 |
| 2012/0271167 | A1 * | 10/2012 | Holland | A61B 8/0833 600/439 |

FOREIGN PATENT DOCUMENTS

| | | | | |
|---|---|---|---|---|
| EP | 0351610 | A2 * | 1/1990 | A61M 37/0092 |
| WO | WO-9829134 | A2 * | 7/1998 | A61M 37/0092 |
| WO | WO-0074767 | A2 * | 12/2000 | A61N 1/327 |
| WO | WO-2021171206 | A1 * | 9/2021 | A61M 37/0092 |

* cited by examiner

*Primary Examiner* — Michael J Tsai
*Assistant Examiner* — Forrest B Dipert
(74) *Attorney, Agent, or Firm* — Faegre Drinker Biddle & Reath LLP

(57) ABSTRACT

Disclosed is a system for therapeutic delivery. The system includes a microneedle patch and an acoustic transducer configured to alter the delivery of the therapeutic from the patch. The acoustic parameters may be determined from a therapeutic release model. The system may also be contained within a housing which may be at least partially removed to deliver the therapeutic. The transducer provides control over the delivery of the therapeutic.

15 Claims, 10 Drawing Sheets

SYSTEMS AND METHODS FOR MICRONEEDLE THERAPEUTIC DELIVERY WITH ACOUSTIC SIGNALS

CROSS-REFERENCE TO RELATED APPLICATION

This application is a 371 U.S. National Phase of International PCT Application No. PCT/US2022/028682, filed May 11, 2022, which claims the benefit of and priority to U.S. Provisional Patent Application Ser. No. 63/187,793, filed May 12, 2021, the dislcosures of which are incorporated herein by reference in their entirety.

FIELD OF THE DISCLOSURE

The devices and methods described herein generally relate to systems and methods for delivering a therapeutic with a microneedle patch and an acoustic signal.

BACKGROUND

A number of commonly used therapeutics are most effectively delivered through injection or transdermal delivery, including therapeutics often administered frequently or by an untrained medical professional. Some examples of such therapeutics are insulin and epinephrine, often used to treat diabetes and anaphylaxis respectively. However, many patients may be uncomfortable injecting themselves or another patient with a therapeutic. A patient may not know when or how to properly administer the therapeutic, which may cause improper delivery. Additionally, many pre-packaged products to be delivered often only have one designated dosage and are not readily adjustable for any given patient.

Additionally, while conventional microneedle patch systems rely on the passive diffusion of encapsulated therapeutics from microneedle tips into the dermis of skin and deeper tissues, it is challenging for microneedle patches to deliver multiple controlled dosages within several short time windows for emergent applications (e.g., treating anaphylaxis).

SUMMARY

What is needed is an improvement over the foregoing. Disclosed herein is a digitalized therapeutic device. Using digital acoustics to control a microneedle patch-mediated drug release, the kinetics of transdermal delivery can be digitally controlled. These devices, systems, and methods can deliver a therapeutic to a patient while controlling the dose, rate, and time of therapeutic delivery, thereby providing a customizable therapeutic delivery that may be adjusted for any set of parameters.

According to an embodiment of the present disclosure, a therapeutic delivery system includes a microneedle patch housing; a microneedle patch supported by the microneedle patch housing and comprising a first side and a second side; an array of microneedles is positioned on the first side of the microneedle patch, the array of microneedles containing a volume of a therapeutic; and an acoustic transducer coupled to the second side of the microneedle patch and configured to generate an adjustable acoustic signal with a plurality of acoustic parameters including a frequency, a duty cycle, an energy density, and a signal delivery time; wherein diffusion of the therapeutic from of the microneedle patch is controllable by altering at least one of the acoustic parameters, and at least one of the acoustic parameters is determined by a therapeutic release model configured to: calculate an acoustic field distribution; calculate a streaming field based on the acoustic field distribution; and calculate the at least one diffusion parameter based on the streaming field, wherein the at least one acoustic parameter is determined based on the at least one diffusion parameter.

In a variation thereof, the at least one diffusion parameter comprises a rate of diffusion. In another variation thereof, the therapeutic comprises at least one of hormones, vaccines, analgesics, phenothiazines, antihistamines, antitussives, and sedatives. In another variation thereof, the microneedle patch is composed of at least one of a polymer and a metal, and the acoustic transducer comprises a piezoelectric material. In still another variation thereof, the frequency is from 0.1 MHz to 10 GHz, the duty cycle is from 0.1% to 100%, the energy density is from 0.1 mW/cm$^2$ to 10.0 W/cm$^2$, and the signal delivery time is from 1 second to 1 hour.

In another variation thereof, the system further comprises a waveform generator operatively coupled to the acoustic transducer and configured to alter the plurality of acoustic parameters. In still another variation thereof, each microneedle in the array of microneedles has a diameter from 0.1 microns to 50 microns, a length from 1 micron to 2 mm, and contains a volume of therapeutic from 0.1 μL to 2 mL, and the microneedle patch has an area from 1 cm$^2$ to 500 cm$^2$. In yet another variation thereof, the therapeutic model comprises a multiphysics simulation. In another variation thereof, the microneedle patch housing is transportable, and the microneedle patch, the acoustic transducer, and a power source operatively coupled to the acoustic transducer are all configured to be contained within the microneedle patch housing. In still another variation thereof, the microneedle patch housing comprises an actuator configured to at least partially remove the microneedle patch from the microneedle patch housing.

According to another embodiment of the present disclosure, a method of delivering a therapeutic includes at least partially removing a microneedle patch from a housing; positioning the microneedle patch on a surface such that a plurality of microneedles penetrate at least a portion of the surface; determining at least one acoustic signal parameter based on a therapeutic release model, the therapeutic release model configured to: calculate an acoustic field distribution; calculate a streaming field based on the acoustic field distribution; and calculate the at least one diffusion parameter based on the streaming field, wherein the at least one acoustic signal parameter is determined based on the at least one diffusion parameter; supplying power to an acoustic transducer coupled to the microneedle patch; generating an acoustic signal comprising the at least one acoustic signal parameter; applying the acoustic signal to the microneedle patch; delivering a volume of the therapeutic through the surface over a delivery time at a delivery rate; and controlling the delivery rate by altering the at least one acoustic signal parameter.

In a variation thereof, the at least one acoustic signal parameter comprises at least one of a frequency, a duty cycle, and an energy density. In another variation thereof, the frequency is adjustable from 0.1 MHz to 10 GHz, the duty cycle is adjustable from 0.1% to 100%, and the energy density is adjustable from 0.1 mW/cm$^2$ to 10.0 W/cm$^2$. In still another variation thereof, delivering step delivers at least 1 μL of a therapeutic over a time of at least 10 minutes. In another variation thereof, the delivery rate is at least two times greater than the delivery rate of a passive microneedle patch without an acoustic signal. In still another variation thereof, the delivering step increases the concentration of therapeutic in the surface by at least 20 mg/mL when the delivery time is at least 6 minutes. In yet another variation thereof, the therapeutic comprises epinephrine and the method further comprises the step of treating anaphylaxis. In another variation thereof, the microneedle patch comprises an array of microneedles arranged in a grid, wherein the grid is from 2×2 to 30×30. In still another variation thereof, the therapeutic is contained within a tip of each of the microneedles in the array of microneedles, and the array of microneedles contains at least 1 μL of the therapeutic. In another variation thereof, the step of at least partially removing the microneedle patch from the hosing is carried out by a mechanical actuator.

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings and replicas of the photographs are not necessarily to scale. In certain instances, details that are not necessary for an understanding of the disclosure or that render other details difficult to perceive may have been omitted. It should be understood, of course, that the disclosure is not necessarily limited to the particular examples or embodiments illustrated or depicted herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
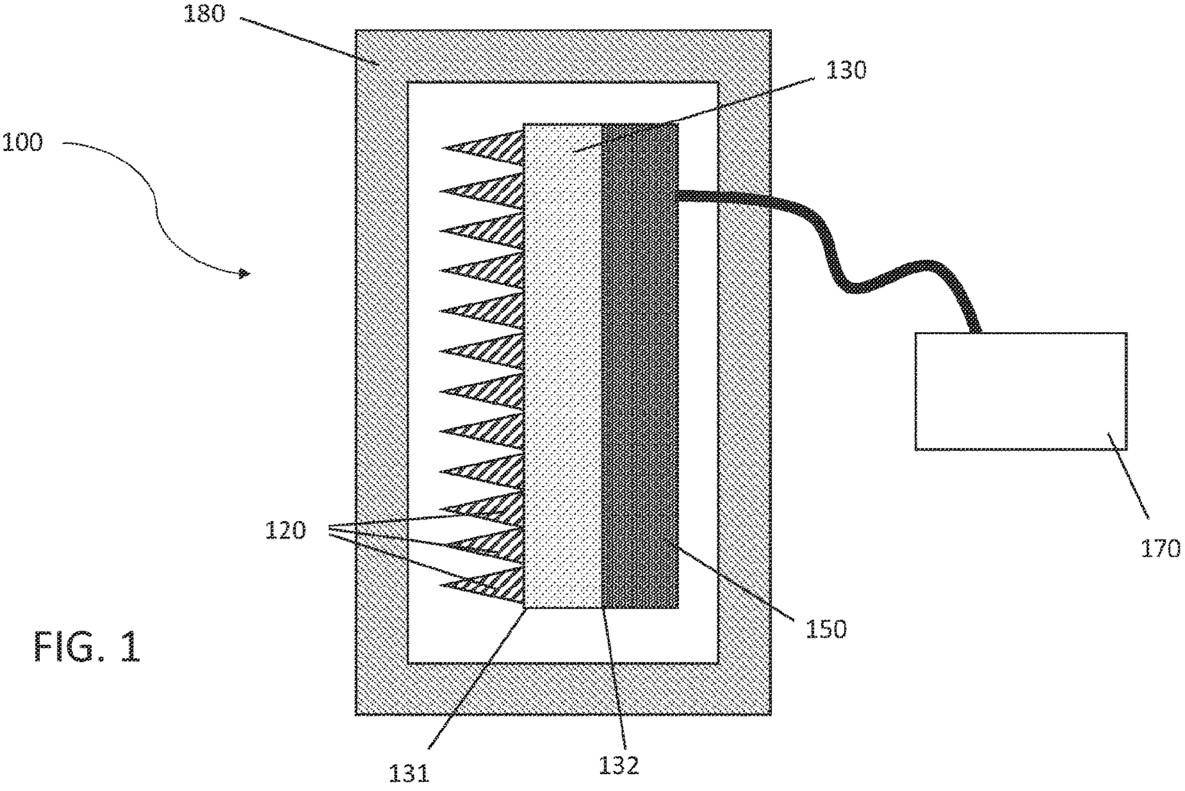
FIG. 1 is a simplified, cross-sectional diagram of a microneedle patch system according to the present disclosure.
Figure 2:
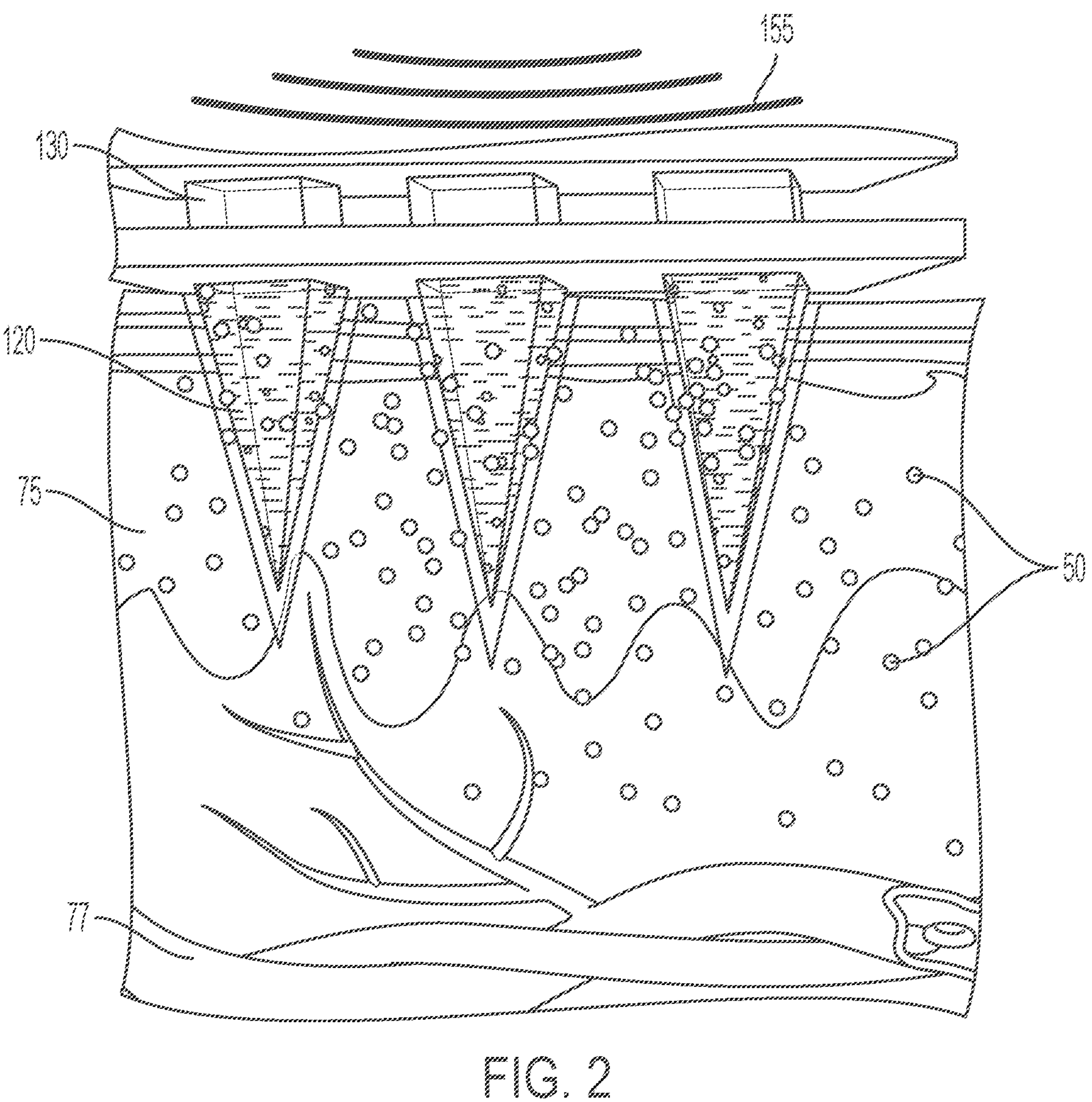
FIG. 2 is a cross-sectional view of a microneedle patch interfacing with a patient's skin.

Referring to FIGS. 1 and 2, an exemplary microneedle system 100 is shown. Microneedle system 100 may also be referred to as a microneedle patch system, a patch system, therapeutic delivery system, or simply a delivery system. Microneedle system 100 comprises a microneedle patch 130 with a number of microneedles 120 (which may be described as an array of microneedles), an acoustic transducer 150, and a housing 180. Acoustic transducer 150 may be operatively coupled to a power supply 170.

Generally, microneedle patch 130 is configured to be positioned against a surface, such as a patient's skin 75, for therapeutic delivery. A volume of a therapeutic 50 is contained within microneedle patch 130. The therapeutic may be contained in the microneedles 120, within a reservoir (not shown), or coated onto a surface of microneedle patch 130 and/or microneedles 120. When positioned against a surface, therapeutic 50 may then diffuse from microneedle patch 130 through the surface to a desired target, such as a patient's blood vessels 77. Acoustic transducer 150 may be utilized to control delivery of therapeutic 50 through the surface by generating an acoustic signal 155, and may alter the delivery dose, delivery rate, and delivery time of the therapeutic delivery through the surface.

Microneedle patch 130 comprises a first surface 131 to which microneedles 120 are coupled, and a second surface 132 to which acoustic transducer 150 is coupled. In some embodiments, acoustic transducer 150 may not be fixedly coupled to microneedle patch 130 and may be placed against the second surface 132 of microneedle patch 130. In other embodiments, acoustic transducer 150 may be placed proximate second surface 132 of microneedle patch 130 such that acoustic signal 155 may still interact with microneedle patch 130 and therapeutic 50, but acoustic transducer 150 may not directly contact microneedle patch 130.

Microneedle patch 130 may be any size or shape configured to interface with a surface. For example, microneedle patch 130 may have an area of 0.1 $cm^2$, 0.5 $cm^2$, 1 $cm^2$, 5 $cm^2$, 10 $cm^2$, 15 $cm^2$, 20 $cm^2$, 25 $cm^2$, 30 $cm^2$, 40 $cm^2$, 50 $cm^2$, 60 $cm^2$, 70 $cm^2$, 80 $cm^2$, 90 $cm^2$, 100 $cm^2$, 125 $cm^2$, 150 $cm^2$, 175 $cm^2$, 200 $cm^2$, 250 $cm^2$, 300 $cm^2$, 350 $cm^2$, 400 $cm^2$, 450 $cm^2$, 500 $cm^2$, 1000 $cm^2$, or any range including any two of these values as endpoints. Microneedle patch 130 may comprise any shape, and may be configured to interface with a specific portion of a patient's body. Microneedle patch 130 may also be flexible in order to conform to a curved surface. Microneedle patch 130 may be composed of any suitable material, such as a polymer, a metal, a composite, and combinations thereof (e.g. a polymer coated metal). In some embodiments, microneedle patch 130 may be composed of a fluoropolymer, polyethylene, polyethylene glycol, polylactic acid, polyglycolic acid, polycarbonate, polyvinyl, polyacrylate, and derivatives, copolymers, emulsions, and mixtures thereof. Microneedle patch 130 may be composed of a biodegradable material such that it may break down over time.

Microneedles 120 may be coupled to microneedle patch 130 through any suitable coupling devices or systems, such as through an adhesive or mechanical coupling features. In an exemplary embodiment, microneedles 120 are integral with microneedle patch 130. Microneedles 120 may be solid, coated, dissolving, hollow, hydrogel-forming, or any combination thereof. In some embodiments, microneedles 120 are configured to directly retain therapeutic 50 for delivery. In other embodiments, microneedles 120 are fluidly coupled to a reservoir containing therapeutic 50 such that therapeutic 50 may be delivered from the reservoir. Microneedle patch 130 and/or microneedles 120 may contain any suitable volume of a therapeutic, for example 0.05 μL, 0.1 μL, 0.15 μL, 0.2 μL, 0.3 μL, 0.4 μL, 0.5 μL, 0.6 μL, 0.7 μL, 0.8 μL, 0.9 μL, 1 μL, 5 μL, 10 μL, 20 μL, 25 μL, 50 μL, 75 μL, 100 μL, 200 μL, 300 μL, 400 μL, 500 μL, 600 μL, 700 μL, 800 μL, 900 μL, 1 mL, 1.25 mL, 1.5 mL, 1.75 mL, 2 mL, 3 mL, 4 mL, 5 mL, or any range including any two of these values as endpoints. Stated differently, microneedle patch 130 and/or microneedles 120 may contain a therapeutic in an amount, for example, from 0.05 μg, 0.1 μg, 0.15 μg, 0.2 μg, 0.3 μg, 0.4 μg, 0.5 μg, 0.6 μg, 0.7 μg, 0.8 μg, 0.9 μg, 1 μg, 5 μg, 10 μg, 20 μg, 25 μg, 50 μg, 75 μg, 100 μg, 200 μg, 300 μg, 400 μg, 500 μg, 600 μg, 700 μg, 800 μg, 900 μg, 1 mg, 1.25 mg, 1.5 mg, 1.75 mg, 2 mg, 3 mg, 4 mg, 5 mg, 6 mg, 7 mg, 8 mg, 9 mg, 10 mg, or any range including any two of these values as endpoints.

Therapeutic 50 may be any therapeutic or biologically active compound, and may be a solid, a liquid, a solution, an emulsion, a suspension, a gel, a powder, or any combination thereof. Therapeutic 50 may comprise, for example, hormones, vaccines, proteins, enzymes, mRNA, anti-inflammatories, stimulants, depressants, analgesics, phenothiazines, antihistamines, antitussives, sedatives, and any derivatives, salts, and combinations thereof. In some embodiments, therapeutic 50 may comprise epinephrine or insulin. Microneedle system 100 may also be configured to delivery non-biologically active compounds, such as tracers or dyes.

Microneedles 120 may be any suitable size and present on microneedle patch 130 in any amount. For example, each microneedle 120 may have a diameter of 0.01 μm (microns), 0.05 μm, 0.1 μm, 0.2 μm, 0.3 μm, 0.4 μm, 0.5 μm, 0.6 μm, 0.7 μm, 0.8 μm, 0.9 μm, 1 μm, 2 μm, 3 μm, 4 μm, 5 μm, 6 μm, 7 μm, 8 μm, 9 μm, 10 μm, 15 μm, 20 μm, 25 μm, 30 μm, 35 μm, 40 μm, 45 μm, 50 μm, 100 μm, 200 μm, 300 μm, 500 μm, or any range including any two of these values as endpoints. Additionally, each microneedle 120 may have a length of 0.5 μm, 0.6 μm, 0.7 μm, 0.8 μm, 0.9 μm, 1 μm, 2 μm, 3 μm, 4 μm, 5 μm, 6 μm, 7 μm, 8 μm, 9 μm, 10 μm, 15 μm, 20 μm, 25 μm, 30 μm, 35 μm, 40 μm, 45 μm, 50 μm, 100 μm, 200 μm, 300 μm, 500 μm, 1 mm, 1.25 mm, 1.5 mm, 1.75 mm, 2 mm, 2.5 mm, 3 mm, or any range including any two of these values as endpoints. Microneedles 120 may also be present in a grid, for example, The grid may be arranged in a pattern of A×B, where A and B may each independently be 2, 3, 4, 5, 6, 7, 8, 9, 10, 11, 12, 13, 14, 15, 16, 17, 18, 19, 20, 30, 40, 50, 60, 70, 80, 90, 100, 125, 150, 175, 200, 300, 400, 500, 1000, or any range including any two of these values as endpoints. Microneedles 120 may also be positioned in any configuration that may not be a symmetrical or ordered grid and may comprise any number of microneedles.

Acoustic transducer 150 is configured to deliver an acoustic signal to microneedle patch 130, microneedles 120, and/or therapeutic 50 to control delivery of therapeutic 50 from microneedle patch 130. As used herein, the term "acoustic" also encompasses "sonic" and "ultrasonic". Acoustic transducer 150 may be any transducer configured to generate an acoustic signal as is known in the art, such as an electromagnetic acoustic transducer, and may comprise piezoelectric components. Acoustic transducer 150 may be composed of a piezoelectric material. Acoustic signal 155 generated by acoustic transducer 150 comprises a plurality of acoustic signal parameters or characteristics, such as a frequency, a duty cycle, an energy density, and a signal time.

The frequency of acoustic signal 155 may be within any suitable acoustic range. For example, the frequency of acoustic signal 155 may be 0.1 MHz, 0.5 MHz, 1 MHZ, 2 MHZ, 3 MHz, 4 MHZ, 5 MHz, 6 MHZ, 7 MHz, 8 MHz, 9 MHZ, 10 MHz, 15 MHZ, 20 MHz, 30 MHz, 40 MHz, 50 MHz, 60 MHz, 70 MHz, 80 MHz, 90 MHz, 100 MHz, 500 MHz, 1 GHz, or any range including any two of these values as endpoints. The duty cycle, which is a percentage of the ratio of pulse duration or pulse width to the total period of a waveform, may be, for example, 0.1%, 1%, 2%, 3%, 4%, 5%, 6%, 7%, 8%, 9%, 10%, 15%, 20%, 25%, 30%, 40%, 50%, 60%, 70%, 80%, 90%, 95%, 100% (continuous), or any range including any two of these values as endpoints. The energy density of acoustic signal 155 may be, for example, 0.1 $mW/cm^2$, 0.5 $mW/cm^2$, 1 $mW/cm^2$, 2 $mW/cm^2$, 3 $mW/cm^2$, 4 $mW/cm^2$, 5 $mW/cm^2$, 6 $mW/cm^2$, 7 $mW/cm^2$, 8 $mW/cm^2$, 9 $mW/cm^2$, 10 $mW/cm^2$, 25 $mW/cm^2$, 50 $mW/cm^2$, 75 $mW/cm^2$, 100 $mW/cm^2$, 200 $mW/cm^2$, 300 $mW/cm^2$, 400 $mW/cm^2$, 500 $mW/cm^2$, 600 $mW/cm^2$, 700 $mW/cm^2$, 800 $mW/cm^2$, 900 $mW/cm^2$, 1 $W/cm^2$, 2 $W/cm^2$, 3 $W/cm^2$, 4 $W/cm^2$, 5 $W/cm^2$, 6 $W/cm^2$, 7 $W/cm^2$, 8 $W/cm^2$, 9 $W/cm^2$, 10 $W/cm^2$, 15 $W/cm^2$, 20 $W/cm^2$, 50 $W/cm^2$, or any range including any two of these values as endpoints. As will be described in more detail herein, the acoustic parameters of acoustic signal 155 may be altered to control delivery of therapeutic 50.

Therapeutic 50 may be delivered through passive diffusion when microneedle patch 130 is positioned on a surface, and the diffusion may be altered by acoustic transducer 150.

In some embodiments, therapeutic 50 may not be delivered until acoustic transducer 150 is activated.

Acoustic transducer 150 may be operatively coupled with a power source 170, a waveform generator, and/or a controller. Each of the power source 170, waveform generator, and controller may be integral in the same unit. Acoustic transducer 150 may operatively couple to other units through, for example, a cable (as shown in FIG. 1) or through wireless communication (e.g. Bluetooth, Wi-Fi, etc.). Acoustic transducer 150 and other units coupled to acoustic transducer 150 may be reusable and may be used with multiple patches. Acoustic transducer 150 may also be removable couplable from other units, such as through a plug. A single power source 170, waveform generator, and/or controller may be usable with multiple transducers and/or patches.

The controller, another processing unit, or the transducer itself may also comprise a therapeutic release model which will be described in more detail herein. Generally, the therapeutic release model is configured to calculate a diffusion parameter and determine an acoustic parameter of acoustic signal 155. The parameters of acoustic signal 155 can be adjusted to alter the delivery of therapeutic 50 from microneedle patch 130. Acoustic signal 155 may oscillate microneedle patch 130 and/or microneedles 120 to increase diffusion rates.

Housing 180 is configured to retain at least one of microneedle patch 130, microneedles 120, acoustic transducer 150, and power supply 170. In some embodiments, each of the aforementioned components are retained within housing 180. In other embodiments, only some of the aforementioned components (e.g. microneedle patch 130, microneedles 120, and acoustic transducer 150) are retained within housing 180, and other components may be positioned outside of housing 180. Housing 180 may be configured such that microneedle system 100 is a transportable assembly. For example, a user may remove a portion of housing 180 to reveal the patch assembly within such that the patch can then be applied to a surface. Housing 180 may comprise flaps, lids, removable seals, adhesives, or any other suitable packaging or housing materials. In some embodiments, a user may punch the microneedle patch through a surface of housing 180 to reveal microneedles 120. The patch may be entirely removed from housing 180 for use or may be partially retained within housing 180 during use. Any components of microneedle system 100 may be configured to be disposable after use. For example, housing 180, microneedle patch 130, and microneedles 120 may be disposable and/or degradable, and acoustic transducer 150 and power supply 170 may be reusable.

Housing 180 may also comprise an actuator to control movement and/or positioning of microneedle patch 130. For example, housing 180 may comprise an acoustic actuator or any other mechanical actuator configured to push at least a portion of microneedle patch 130 out of housing 180 and onto a surface. The actuator may control the depth of penetration of microneedles 120 into the surface, as well as the pressure applied to the microneedle patch 130 and the time of application. The housing 180 and/or actuator may also remove the microneedle patch 130 from the surface after a time has passed. The housing 180 may be pressed up against a surface, and then the actuator may be activated to at least partially remove microneedle patch 130 from the housing and position microneedle patch 130 on the surface. The microneedle patch 130 may then be retracted at least partially into housing 180 after a time has passed.

Microneedle system 100 may comprise sensors (not shown) to monitor patient conditions or conditions related to microneedle system 100 prior to, during, and/or after delivery of therapeutic. For example, microneedle system 100 may comprise a sensor to monitor a patient's heart rate, blood oxygen concentration, hormone levels, blood glucose levels, blood pH, or any other suitable criteria. Additionally, sensors may measure how much of a therapeutic has been delivered, rate of delivery, how long the therapeutic has been delivered, or acoustic parameters of acoustic signal 155. Sensor data may then be used to control acoustic transducer 150. For example, if the rate of delivery is sensed to be below a target rate, acoustic transducer 150 may alter acoustic parameters to increase delivery rate. If microneedle system 100 is being used to treat a specific condition (e.g. anaphylaxis), sensors may monitor a patient condition and deliver a therapeutic until indication of the condition subsides or is reduced.

Microneedle system 100 may comprise delivery indicators (not shown) to indicate to a patient when the therapeutic has been delivered. Delivery indicators may comprise a light, a screen, a color-changing component, a sonic indicator, or any other suitable indicator to provide information related to the delivery of the therapeutic to the patient. Microneedle system 100 may also comprise additional features not illustrated, such as an insulating backing behind acoustic transducer 150, an adhesive to improve adhesion of the patch to a surface, electrical connections, batteries, sensors, printed indicia (e.g. instructions for use, indications as to which therapeutic is present, etc.), and any combination thereof.

Figure 3:
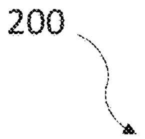
FIG. 3 is a flowchart for a method of delivering a therapeutic with the microneedle patch system of FIG. 1.
Figure 3:
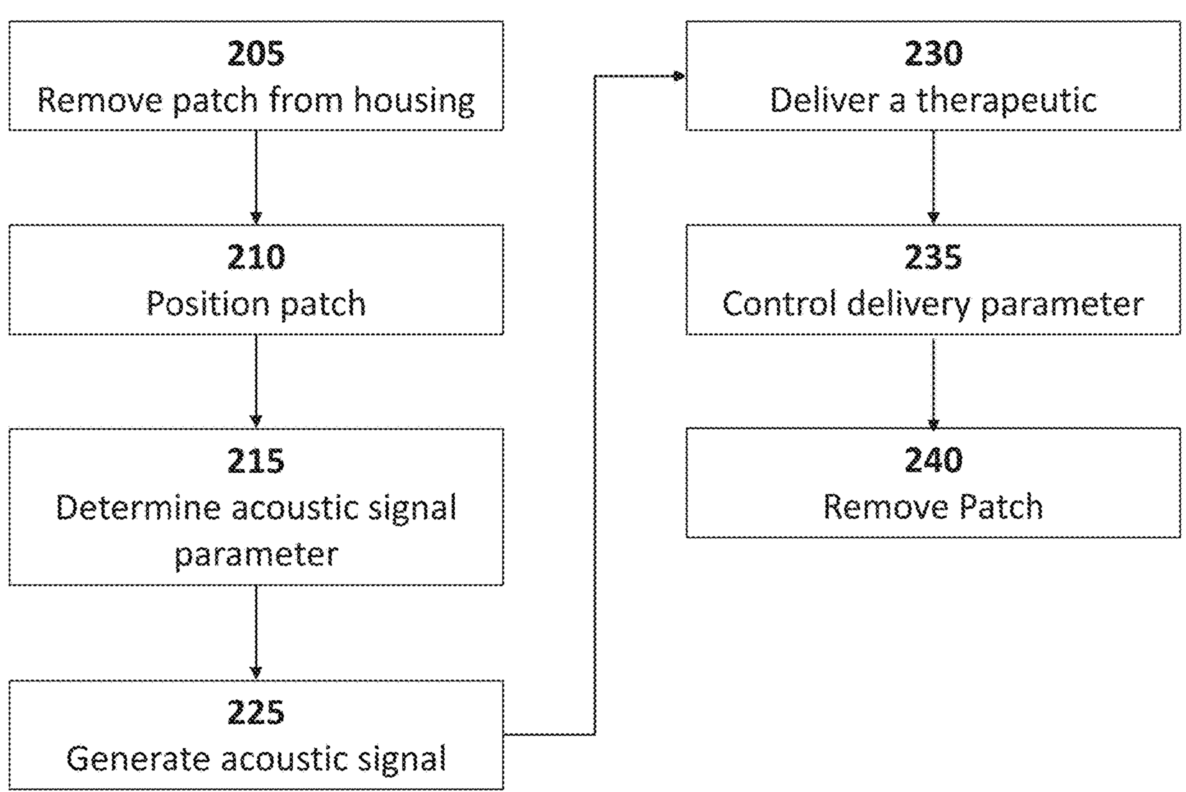

Referring now to FIG. 3, a method 200 for delivering a therapeutic is shown. The method comprises a removal step 205, a positioning step 210, a determining step 215, a generating step 225, a delivering step 230, a controlling step 235, and a removal step 240. During removal step, a user removes at least a portion of microneedle patch 130, microneedles 120, acoustic transducer 150, and/or power supply 170 from housing 180 as described above. In positioning step 210, the user may then position the patch on a surface, such as a patient's skin such that microneedles 120 interface with the surface.

Figure 4:
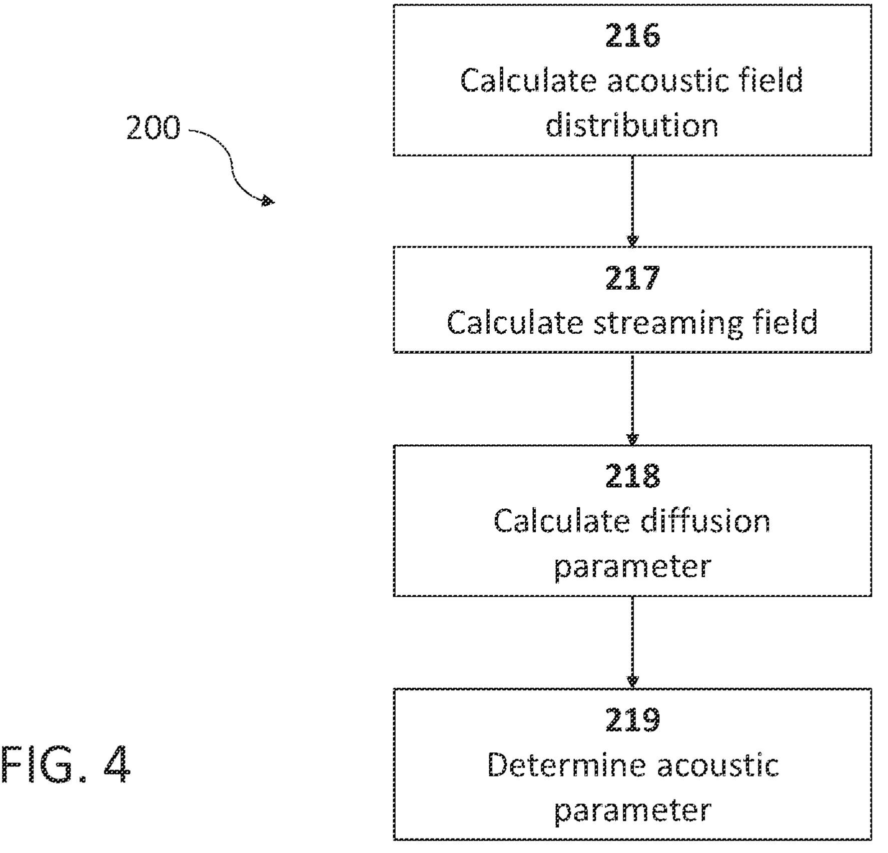
FIG. 4 is a flowchart for a method of determining an acoustic parameter with a therapeutic delivery model.

Determining step 215 is shown in more detail in FIG. 4. Determining step 215 may be carried out, at least partially, by a therapeutic release model, which may also be referred to as a diffusion model, an acoustic diffusion model, a therapeutic delivery model, or an acousto-fluidics model. Therapeutic release model comprises at least a partial simulation of the therapeutic delivery and is configured to determine diffusion parameters of the therapeutic and parameters of the acoustic signal. In general, the therapeutic model is configured to calculate 216 an acoustic field distribution, calculate 217 a streaming field based on the acoustic field distribution, calculate 218 a diffusion parameter based on the streaming field, and determine 219 an acoustic parameter based on the diffusion parameter. Calculating steps 216 and 217 may be optional, and the therapeutic release model may comprise additional and/or alternative methods for determining acoustic parameters. Stated differently, therapeutic release model may not calculate an acoustic field distribution and/or a streaming field. Any suitable model may be utilized to calculate diffusion and acoustic parameters. One embodiment of a therapeutic release model may function as follows:

The governing perturbation equations for the acoustic fields in the porous media consist of balance of linear momentum and balance of mass. Considering the effects of the 2-phase porous structure, the standard equation of porous medium dynamics can be written as:

$$\rho\left(\frac{\partial v}{\partial t} + v \cdot \nabla v\right) = -\nabla p - \gamma w$$

$$\frac{\partial}{\partial t}(\phi\rho) + \nabla \cdot (\phi\rho v) = 0$$

$$w := \phi(v - u)$$

The actual density of the fluid is ρ, the volume fraction of porous media is ϕ, the interstitial fluid velocity is v, $\gamma \equiv 1/K$ is the inverse of the hydraulic conductivity K, u is the velocity of the porous solid frame, and w is the relative velocity of fluid. Under harmonic force, the motion of fluidic is generally not harmonic and generally composes two components: 1) a first order component of the same periodic to the activation force, 2) a second order stable component (acoustic streaming). Taking the first and second order into account, we can write:

$$w = w_1 + w_2$$

$$v = v_1 + v_2$$

$$u = u_1 + u_2$$

$$\rho = \rho_0 + \rho_1 + \rho_2$$

$$p = p_0 + p_1 + p_2$$

$$\phi = \phi_0 + \phi_1 + \phi_2$$

For the first order equation, we assume that acoustic waves travel in a uniform media, and the fluid and porous frame move together with same velocity. Thus, $w_1$ and $\phi_1$ vanish in the first order equation, thus we can get:

$$\frac{\partial \rho_1}{\partial t} + \rho_0(\nabla \cdot v_1) = 0$$

$$\rho_0\left(\frac{\partial v_1}{\partial t} + v_1 \cdot \nabla v_1\right) = -\nabla p_1$$

For the second order equation, since there is no streaming in porous frame, the second order frame velocity $u_2$ is zero. Expanding the equation to the second order and average the equation over a cycle yields:

$$\gamma w_2 = -\nabla p_2 - \rho_0 \nabla \cdot \langle v_1 v_1 \rangle$$

$$\nabla \cdot w_2 = -\phi_0 \frac{\nabla \cdot \langle \rho_1 v_1 \rangle}{\rho_0}$$

The second order equation has a form of Darcy's law, supplemented with a streaming force term. For the acoustic enhanced convection diffusion of dye and drug, the governing equation is conventional diffusion equation:

$$\frac{\partial c}{\partial t} = \nabla \cdot (D\nabla c) - \nabla(v^c c) + R$$

where c is the species concentration, D is the diffusivity, $v^c$ is the velocity field that the quantity is moving with. R describes sources or sinks of the quantity c.

To reduce the computational effort, one needle may be solved for in periodic needle array on 2D, because the needles' vibration may be periodic in both the x- and y-directions. Based on the above-mentioned theoretical derivation, the numerical procedure is divided in three steps (FIG. 4): solving 216 the acoustic field (1st-order problem) in the porous media domain; (b) solving 217 the 2nd-order problem in porous domain based on the 1st-order result from the former step and obtaining the streaming field; and (c) solving 216 diffusion of dye in porous domain assisted by acoustic streaming. A Multiphysics simulation, such as COMSOL 5.3a (the COMSOL Group) may be employed for the calculation according to the above-mentioned steps. In step (a), the predefined "Pressure acoustics" modified with "Poroacoustics" physics may be used to calculate acoustic field distribution (1 st-order problem) in porous media. A "Periodic" boundary condition, which confines periodic connection of needles in the array and fluidic domain, may be applied to side two boundaries of porous domain. To eliminate wave reflection, top boundary was set as the "normal impedance" equal to that of the porous media. An activation of defined periodicity may be applied to the patch boundary to account for acoustic vibration. Based on these settings, a "Frequency Domain" solver may be used to solve the abovementioned physics together at the driving frequency. In step (b), the "Darcy's law" physics may be used to solve the 2nd-order problem (Acoustic streaming) in porous media. The mass and force source terms may be imposed by adding "weak contribution" and "volume force" conditions, respectively. Similarly, which confines periodic connection of needles in the array and fluidic domain, ma be applied to two surrounding boundaries. And an "outlet" boundary condition, which indicates no pressure difference on the two sides of a boundary, may be imposed to the media-media interfaces. This physics may be solved via a "Stationary" solver by using the 1st-order solution of the previously mentioned "Frequency Domain" solver. As the last step, the "Transport of Diluted Species" were used to solve the diffusion problem of dye. A constant concentration of therapeutic may be set on the surface of patch to account for the diffusion. All the walls of porous media may be set as no flux boundary condition. These physics may be solved via a "Time Dependent" solver in total of any amount of time with any interval (e.g. 100 s with interval of 0.1 s) by using the 2nd-order solution of the previously mentioned "Stationary" solver.

Combining the aforementioned second-order equation yields:

$$\nabla^2 p_2 = \nabla \cdot \left(-\rho_0 \nabla \cdot \langle v_1 v_1 \rangle + \frac{\gamma \phi_0}{\rho_0} \langle \rho_1 v_1 \rangle\right)$$

Thus, the streaming speed in the porous media also may have the estimated relation with acoustic pressure:

$$v_{porous} \sim \omega P^2$$

This streaming results in an effective diffusivity:

$$D_{eff} \sim \omega P^2$$

If the convection diffusion to 1D diffusion is simplified from the patch to the porous media, with a consistent concentration co at the surface of the patch, this yields:

$$\frac{\partial c}{\partial t} = D\frac{\partial^2 c}{\partial x^2}$$
$$D = D_0 + D_{eff}$$

where $D_0$ is the diffusivity of dye in the porous media. The regulation of this estimation equation is:

$$c = 0 \text{ at } t = 0$$
$$c = c_0 \text{ at } t = 0$$

With a solution:

$$c(x, t) = c_0\left[1 - \text{erf}\left(\frac{x}{\sqrt{4Dt}}\right)\right]$$
$$D = D_0 + D_{eff}$$
$$D_{eff} \sim \omega P^2$$

Integrating along x to get d (the total released therapeutic mass) on time t yields:

$$d = c_0\sqrt{\frac{4Dt}{\pi}}$$
$$D = D_0 + D_{eff}$$
$$D_{eff} \sim \omega P^2$$

The therapeutic model described above may be used to calculate a diffusion parameter. The diffusion parameter may comprise a total delivery dose or a delivery rate. The diffusion parameters may be altered for any given patient, therapeutic, or microneedle patch system. For example, a younger or smaller patient may require less of a dose than an older or larger patient, so the diffusion parameter may be altered to deliver a desired dose. Additionally, a given therapeutic may be more effective if delivered quickly instead of slowly, so the diffusion parameter may be adjusted based on the desired delivery rate. The relationship derived from the diffusion parameter and the acoustic parameters allows for determining of the acoustic parameters for a given delivery. For example, the therapeutic release model may calculate the acoustic parameters required for a desired delivery rate.

Referring back to FIG. 3, once the acoustic signal parameters are determined from the therapeutic release model, the acoustic signal is then generated in generating step 225, comprising the acoustic parameters determined in step 215. For example, if therapeutic model determined a certain frequency, energy density, duty cycle, and delivery time to achieve a desired delivery rate, the acoustic transducer may then generate a signal with those parameters. The signal is then applied to microneedle patch 130, microneedles 120, and/or therapeutic 50 to alter diffusion of the therapeutic. Delivering step 230 comprises delivering the therapeutic to a surface. Delivering step may increase a concentration of therapeutic at a location proximate microneedles 120, and may deliver a therapeutic to blood vessels or another organ of a patient.

Controlling step 235 comprises altering a part of acoustic signal 155 to alter a delivery parameter of therapeutic, such as a delivery rate, a delivery dose, and/or a delivery time. For example, acoustic signal 155 may be stopped once a target dose has been delivered. Additionally, sensor feedback may cause altering of acoustic signal 155 to increase or decrease delivery rate, dose, or time. Controlling step 235 may comprise continuously calculating diffusion and/or acoustic parameters through the therapeutic release model. Removing step 240 comprises removing the patch from a surface. For example, as described above, an actuator and/or housing 180 may remove microneedle patch 130 from contact with a patient's skin. Once removed, the patch may stop delivering a therapeutic to a patient. Controlling step 235 and removing step 240 may be combined in one step. For example, delivery time may be controlled by removing microneedle patch 130 from a surface.

In summary, a therapeutic delivery system comprises a microneedle patch with an array of microneedles and an acoustic transducer configured to deliver an acoustic signal to alter the delivery of the therapeutic from the patch. The acoustic signal may have parameters determined by a therapeutic release model, such that the delivery of the therapeutic may be controlled and adjusted for any given patient, therapeutic, or patch system. Any of the components of the delivery system may be contained within a housing and may be removed for use.

EXAMPLES

Acoustic Microneedle Patch Overview

In the following examples, which will be described in more detail, an acoustic microneedle patch was developed for digital transdermal delivery via the programed acoustic stimulations. Our acoustic patch consists of two components including a PEGDA-based microneedle patch device with therapeutics loaded microneedle tips (12×12) and a piezoelectric transducer (PZT) to generate programmable acoustic waves. After penetrating microneedle tips through the epidermis of skin, the acoustic patch can release encapsulated therapeutics from microneedle tips into the dermis of skin and deeper tissues with controlled rate, dose, and duration by introducing programmed acoustic vibration and streaming. Different from microneedle patch, our acoustic patch provides an active transdermal delivery method to digitally release or enhance the encapsulated therapeutics.

Fabrication of Microneedle Patch

The poly (ethylene glycol) diacrylate (PEGDA)-based microneedle patches loaded with sulforhodamine B (RhB, Sigma-Aldrich, MO) or epinephrine (Sigma-Aldrich, MO) were fabricated using polydimethylsiloxane moulds (Micropoint Ltd., Singapore). The former solution was prepared by well mixing 0.89 mL of PEGDA (MW 700, Sigma-Aldrich, MO), 10 mg of Irgacure 2959 dissolved in 10 μL of DMSO, and 0.1 mL of 25 mg/mL RhB solution (or 621 μg of epinephrine). The latter solution was prepared by well-mixing 0.99 mL of PEGDA, and 10 mg of Irgacure 2959 dissolved in 10 μL of DMSO. Then, the former solution was loaded into microneedle mold, treated within vacuum for 5 minutes to fill the solution into the microneedle tip reservoirs. Then, extra former solution was wiped away from the surface of the microneedle mold. The latter solution was immediately added onto the microneedle mold and degassed for 5 minutes. Then, the microneedle mold was covered with a piezoelectric transducer and exposed to UV light (365 nm) for 1.5 mins. Finally, the polymerized PEGDA microneedle patch was carefully removed from the moulds. The morphology of the microneedles was characterized by using a Leica stereomicroscope (M205FA, Germany).

In Vitro Delivery in Agar

The digital (or passive) release performance was characterized after removing the RhB dye (or epinephrine) on the microneedle surfaces. We washed the microneedle surfaces by inserting RhB dye (or epinephrine) loaded microneedles into an agar gel (length: 1 cm, width: 1 cm, thickness: 1 mm) for 30 seconds (without acoustic treatment). The washed patches were inserted into a piece of dry agar gel (length: 1 cm, width: 1 cm, thickness: 1 mm), followed by the acoustic treatment (frequency, 1 Mhz; duty cycle, 15%; energy density, 0 to 5.8 w/cm$^2$; time, 0 to 10 mins), and removed from the gel. The amount of the released RhB dye was calculated based on the standard fluorescence curve.

Ex Vivo Delivery in Mice

The prepared RhB dye (or epinephrine) loaded acoustic patches (or passive patches) were inserted into the fresh hair removed skin tissues harvested from BALB/c mice, and removed from the mice skin tissues. The acoustic path treatment condition (frequency, 1 Mhz; duty cycle, 15%; energy density, 4.2 w/cm$^2$) was applied to three mouse skin tissues, while there was not acoustic stimulation for passive patch treatments. The mouse skin tissues after acoustic patch and passive treatments with three different treatment time (e.g., 30 s, 60 s, or 180 s) were analyzed.

In Vivo Delivery in Mice

12 C57BL/6J mice were used to compare in vivo acoustic patch-enabled digital release to subcutaneous injection, passive release, and bank control using an in vivo imaging system (IVIS Spectrum, Perkin Elmer). The furs on the back of mice were removed by Nair® hair removal lotion one day before the experiment. The mice were anesthetized and administrated RhB dye in four different groups including (1) acoustic patch group (frequency, 1 Mhz; duty cycle, 15%; energy density, 4.2 w/cm$^2$) (2) passive patch group; (3) subcutaneous injection; and (4) blank group (without any treatment). After washing skin surface three times with PBS-soaked cotton balls, the mice were imaged at each pre-determined time point (10 mins, 60 mins, and 240 mins). At 24 hours, the mice were euthanized and the organs (e.g., liver, spleen, muscle and skin) were dissected and visualized by the IVIS imaging system to study the biodistribution of dye RhB.

Treatment of Anaphylaxis

An active systemic anaphylaxis (ASA) model was established by following reported protocols. Olbumin from chicken egg white (OVA) was used as antigen to induce anaphylaxis, where OVA dosage could regulate the degree of anaphylaxis. Specifically, an OVA solution as an adjuvant was prepared in 1 mg/mL of OVA with 1 μg/mL of Pertussis toxin and 10 mg/mL of aluminum potassium sulfate in 0.9% saline. To sensitize mice, BALB/c mice were injected intraperitoneally with 100 μL of the adjuvant OVA solution. After 3 weeks, these actively sensitize mice were challenged with 10 mg/mL of the adjuvant OVA solution. To trigger the anaphylactic reaction, a 50 μL of 10 mg/mL OVA solution in 0.9% saline was injected intraperitoneally into a mouse. The whole anaphylactic process lasted for about 120 mins, and all the mice were sacrificed after the experimental procedures.

The mice during anaphylaxis were characterized via physiological parameters and symptoms including rectal temperature, movement score, respiratory rate, or blood histamine level. Rectal temperature was measured using a rectal probe for mice in every 2 min in real-time. Respiratory rate was measured through counting the breaths during every 20 seconds through observing the thoracic movement. Movement score was tested by rules as follows: (1) react actively after provoking; (2) slow in response after provoking; (3) no active response after provoking; (4) died. Blood histamine level was measured by testing whole blood samples through tail vein through an ELISA kit (Catalog No: IT6088, vendors). Samples were all restored in −80° C. refrigerator for later assessment of the concentration of histamine by an ELISA kit.

The anaptyctic mice were recused by administrating epinephrine via needle injection or patch treatment. Epinephrine was dissolved by 0.9% saline to reach a concentration of 80 μg/ml and 160 μg/ml. For the needle injection, the epinephrine solution was loaded in a syringe ((27G needles; 1 ml Syringes, BD) and then injected through thigh intramuscular injection. For the patch treatment, the epinephrine-loaded microneedle patch was insert into the back of a mouse with removed hair, and treated using different acoustic stimulation conditions.

Statistical Analysis

The statistics comparing two sample groups were conducted using the Students' t-test. Statistical significance was denoted as following: *p<0.05, p<0.01, *p<0.005. ****p<0.001

Theoretical Model

The theoretical therapeutic release model used is the same as described above, configured to calculate diffusion parameters.

Results and Discussion

Figure 5:
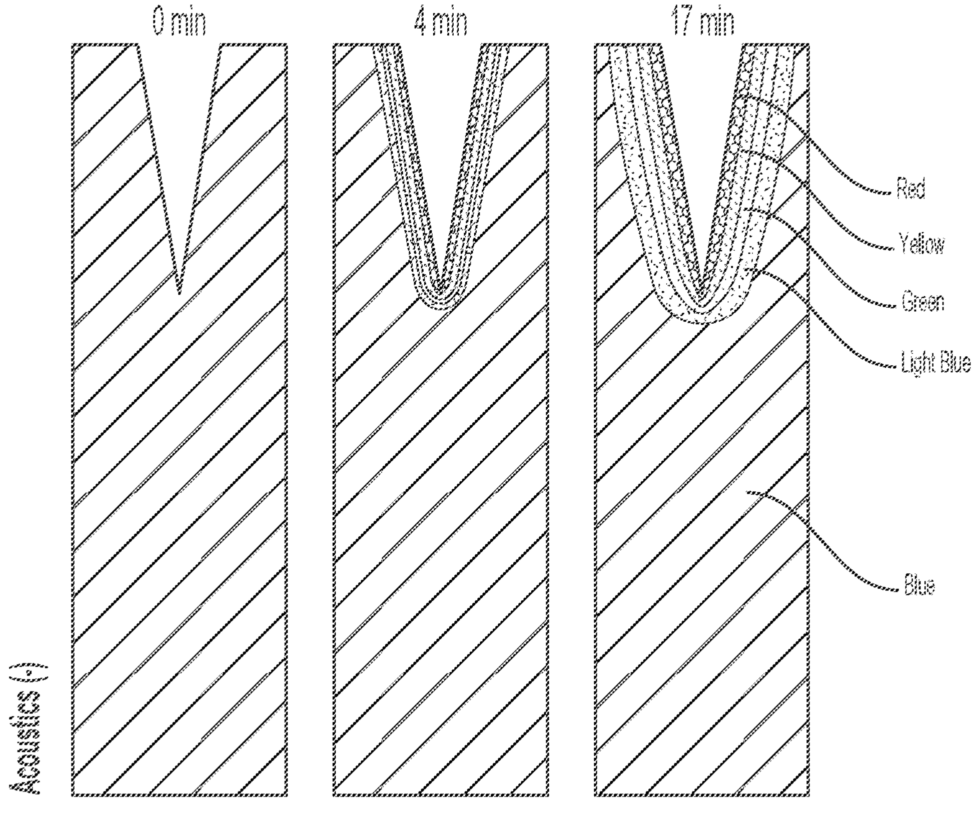
FIGS. 5 and 6 are simulated concentration profiles of a therapeutic diffusing from a microneedle without acoustics and a microneedle with acoustics, respectively.
Figure 6:
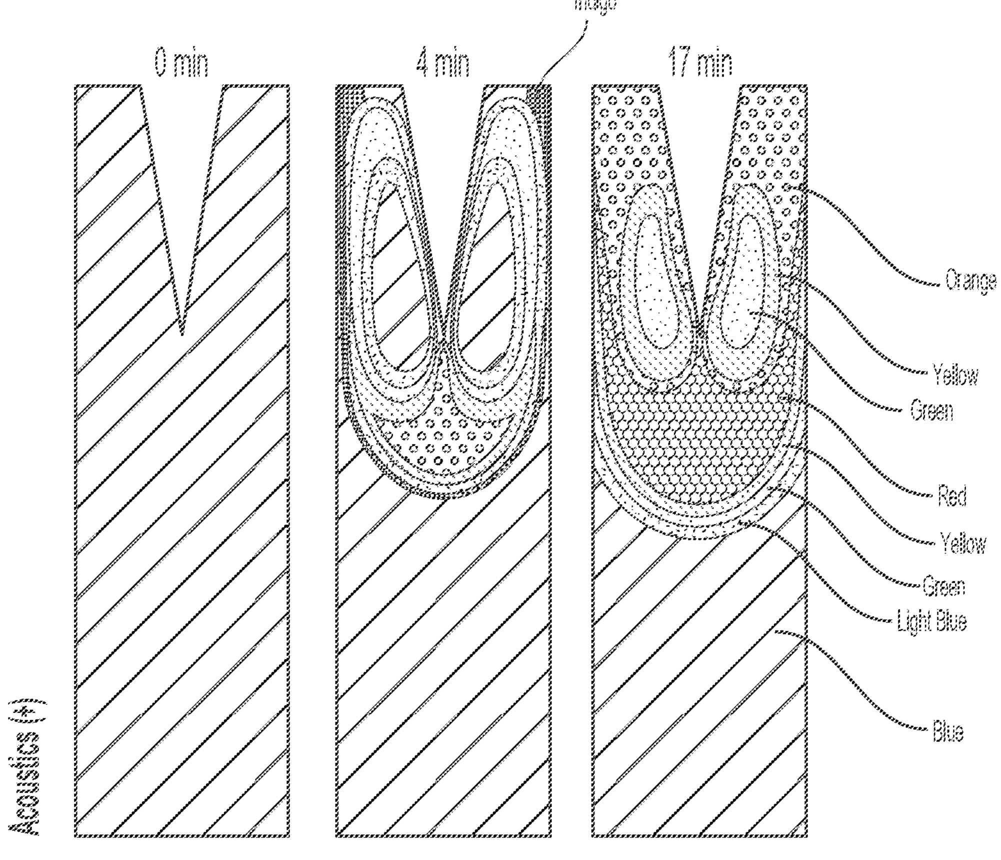
Figure 7:
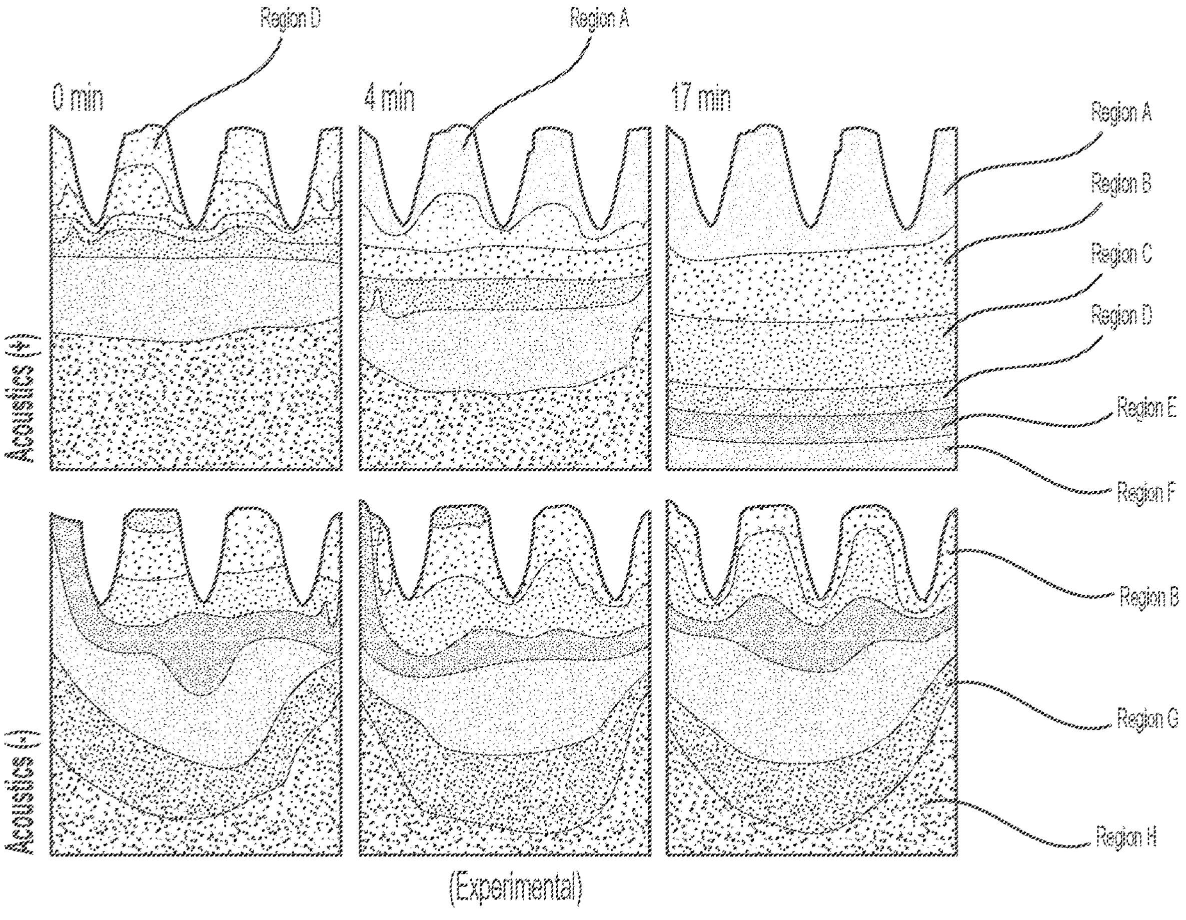
FIG. 7 is an experimental concentration profile over time of a fluorescent dye diffusing from a microneedle patch without acoustics and with acoustics.

Referring to FIGS. 5 and 6, simulated diffusion profiles of a therapeutic are shown in exemplary microneedles without acoustics (−) and with acoustics (+) respectively. The simulation was completed by the therapeutic release model as described above. In these figures, each region is marked by a color in the spectrum, e.g. red, orange, yellow, green, light blue, indigo, and blue, with each pattern representing the same color. The rate of diffusion is the greatest in the red region, followed by orange, yellow, green, light blue, indigo, and blue in descending order. As shown, not only do acoustic signals increase the rate of diffusion, but they also provide a relatively uniform distribution in the medium. FIG. 7 shows an experimental microneedle system that shows similar results to the simulation. RhB dye is shown released over time into an agar gel, and again the acoustics provided an increase in delivery rate. FIG. 7 shows a plurality of regions, each with its specific intensity in the brightness of the RhB dye, as shown. The brightest-colored region is Region A, and the darkest-colored region is Region H, with Regions B through G located therebetween in descending order of brightness.

Figure 8:
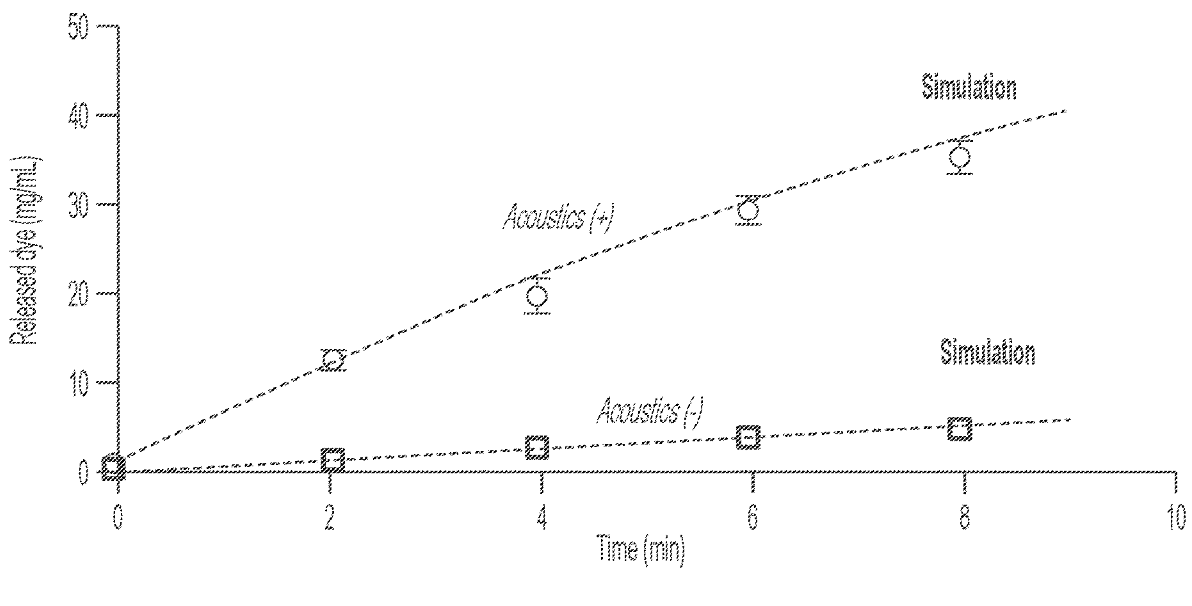
FIG. 8 is a plot of released dye concentration as a function of time, for simulated and experimental microneedle patches with and without acoustics.

FIG. 8 shows a plot of dye released (concentration) as a function of delivery time for a microneedle patch with and without acoustics, both experimentally and theoretically. As shown, the acoustic patch delivers a therapeutic at a faster rate than the non-acoustic patch, and the theoretical values from the therapeutic release model approximately match the values shown experimentally. An acoustic patch system as described may increase the concentration of a therapeutic in a surface or medium by at least 5 mg/mL, at least 10 mg/mL, at least 20 mg/mL, at least 25 mg/mL, at least 30 mg/mL, at least 40 mg/mL, at least 50 mg/mL, or any range including any two of these values as endpoints over the course of at least 1 minute, at least 2 minutes, at least 3 minutes, at least 4 minutes, at least 5 minutes, at least 6 minutes, at least 7 minutes, at least 8 minutes, at least 9 minutes, at least 10 minutes, or any range including any two of these values as endpoints. Compared to a non-acoustic patch, an acoustic patch may increase the delivery rate by at least 1.1 times, at least 1.2 times, at least 1.3 times, at least 1.4 times, at least 1.5 times, at least 1.6 times, at least 1.7 times, at least 1.8 times, at least. 1.9 times, at least 2 times, at least 2.1 times, at least 2.2 times, at least 2.3 times, at least 2.4 times, at least 2.5 times, at least 3 times, or any range including any two of these values as endpoints.

Figure 9:
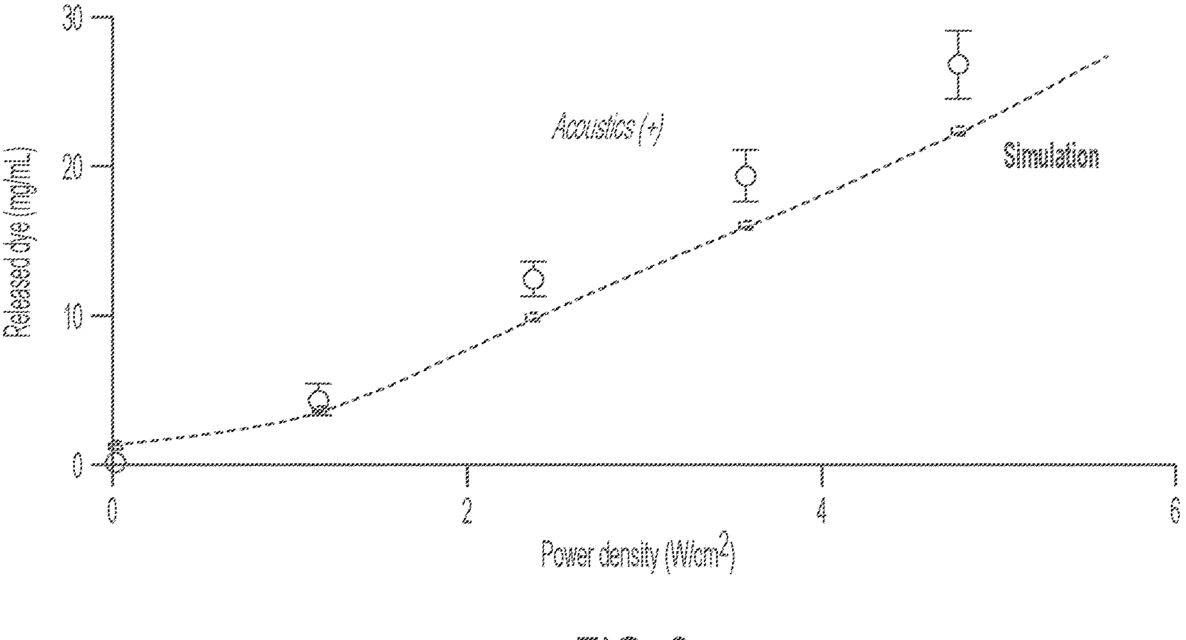
FIG. 9 is a plot of released dye concentration as a function of acoustic power density for simulated and experimental microneedle patches with acoustics.

Referring now to FIG. 9, dye released is shown as a function of power density, again demonstrating that the theoretical release model approximates experimental values and may be used to determine acoustic parameters in practice. The data for FIGS. 7-9 were collected by delivering RhB fluorescent dye in agar gel.

Figure 10:
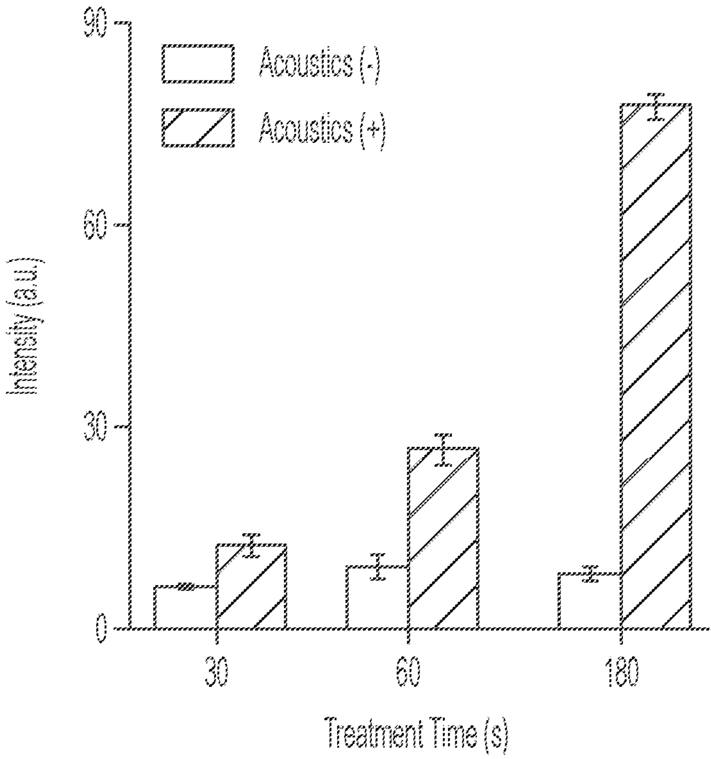
FIG. 10 is a plot of absorbance values for dye released into mice skin as a function of treatment time.

FIG. 10 shows a quantification of dye released when delivering RhB fluorescent dye into mouse skin over different delivery times with and without acoustics. The acoustics again demonstrated increased delivery and illustrated effectiveness in living tissue.

An anaphylactic mouse model was also established in mice using well-developed protocols, approved by Indiana University animal protocol (#19-006). Mice were sensitized via intraperitoneal injection of chicken ovalbumin (OVA) and aluminum potassium sulfate adjuvant and triggered an acute allergic reaction by injecting OVA as an allergen after three weeks. The established anaphylactic mice show symptoms, including hypothermia, reduced activity, and opisthotonos. After intramuscular injection of epinephrine, the anaphylaxis mice obtained relief from these symptoms. We measured the core temperature and respiratory rate of the sensitized mice during the induction of anaphylaxis. The mouse "A" experienced rapid body temperature drops and then died after a severe allergic reaction; the mouse "B" experiencing severe anaphylaxis had a quick body temperature drop and an immediate body temperature increase after the acoustic patch mediated epinephrine delivery, and finally relief from allergic symptoms; the heathy mouse had a stable body temperature. Meanwhile, the anaphylactic mice showed reduced respiration once they received OVA inductions. These results demonstrated that anaphylaxis can be effectively modeled and relief from anaphylaxis by delivering epinephrine can be achieved with the acoustic patches described herein. Physiological conditions and variations thereof can also be monitored, allowing for increased delivery control.

Various modifications and additions can be made to the embodiments disclosed herein without departing from the scope of the disclosure. For example, while the embodiments described above refer to particular features, the scope of this disclosure also includes embodiments having different combinations of features and embodiments that do not include all of the described features. Thus, the scope of the present disclosure is intended to embrace all such alternatives, modifications, and variations as fall within the scope of the claims, together with all equivalents.

All publications, patents and patent applications referenced herein are hereby incorporated by reference in their entirety for all purposes as if each such publication, patent or patent application had been individually indicated to be incorporated by reference. Specifically, the following publication, including its supporting information, which is attached hereto as Exhibit A, is incorporated by reference in its entirety: "An Acoustic Microneedle Patch for Digital Transdermal Delivery", Xu, Junhua et al, Department of Intelligent Systems engineering, Indiana University, Bloomington, IN.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A therapeutic delivery system comprising:

a microneedle patch housing;

a microneedle patch supported by the microneedle patch housing and comprising a first side and a second side;

an array of microneedles is positioned on the first side of the microneedle patch, the array of microneedles containing a volume of a therapeutic; and an acoustic transducer coupled to the second side of the microneedle patch and configured to generate an adjustable acoustic signal with a plurality of acoustic parameters including a frequency, a duty cycle, an energy density, and a signal delivery time;

wherein diffusion of the therapeutic from of the microneedle patch is controllable by altering at least one of the acoustic parameters, and at least one of the acoustic parameters is determined by a therapeutic release model configured to:

calculate an acoustic field distribution;

calculate a streaming field based on the acoustic field distribution; and calculate the at least one diffusion parameter based on the streaming field, wherein the at least one acoustic parameter is determined based on the at least one diffusion parameter.

2. The therapeutic delivery system of claim 1, wherein the at least one diffusion parameter comprises a rate of diffusion.

3. The therapeutic delivery system of claim 1, wherein the therapeutic comprises at least one of hormones, vaccines, analgesics, phenothiazines, antihistamines, antitussives, and sedatives.

4. The therapeutic delivery system of claim 1, wherein the frequency is from 0.1 MHz to 10 GHz, the duty cycle is from 0.1% to 100%, the energy density is from 0.1 $mW/cm^2$ to 10.0 $W/cm^2$, and the signal delivery time is from 1 second to 1 hour.

5. The therapeutic delivery system of claim 1, further comprising a waveform generator operatively coupled to the acoustic transducer and configured to alter the plurality of acoustic parameters.

6. The therapeutic delivery system of claim 1, wherein each microneedle in the array of microneedles has a diameter from 0.1 microns to 50 microns, a length from 1 micron to 2 mm, and contains a volume of therapeutic from 0.1 μL to 2 mL, and the microneedle patch has an area from 1 $cm^2$ to 500 $cm^2$.

7. The therapeutic delivery system of claim 1, wherein the therapeutic model comprises a multiphysics simulation.

8. The therapeutic delivery system of claim 1, wherein the microneedle patch is composed of at least one of a polymer and a metal, and the acoustic transducer comprises a piezoelectric material; the microneedle patch housing is transportable, and the microneedle patch, the acoustic transducer, and a power source operatively coupled to the acoustic transducer are all configured to be contained within the microneedle patch housing; or the microneedle patch housing comprises an actuator configured to at least partially remove the microneedle patch from the microneedle patch housing.

9. A method of delivering a therapeutic comprising the steps of:

at least partially removing a microneedle patch from a housing;

positioning the microneedle patch on a surface such that a plurality of microneedles penetrate at least a portion of the surface;

determining at least one acoustic signal parameter based on a therapeutic release model, the therapeutic release model configured to:

calculate an acoustic field distribution;

calculate a streaming field based on the acoustic field distribution; and calculate the at least one diffusion parameter based on the streaming field, wherein the at least one acoustic signal parameter is determined based on the at least one diffusion parameter;

supplying power to an acoustic transducer coupled to the microneedle patch;

generating an acoustic signal comprising the at least one acoustic signal parameter;

applying the acoustic signal to the microneedle patch;

delivering a volume of the therapeutic through the surface over a delivery time at a delivery rate; and controlling the delivery rate by altering the at least one acoustic signal parameter.

10. The method of claim 9, wherein the at least one acoustic signal parameter comprises at least one of a frequency, a duty cycle, and an energy density.

11. The method of claim 10, wherein the frequency is adjustable from 0.1 MHz to 10 GHz, the duty cycle is adjustable from 0.1% to 100%, and the energy density is adjustable from 0.1 $mW/cm^2$ to 10.0 $W/cm^2$.

12. The method of claim 9, wherein the microneedle patch comprises an array of microneedles arranged in a grid, wherein the grid is from 2×2 to 30×30.

13. The method of claim 12, wherein the therapeutic comprises epinephrine and the method further comprises the step of treating anaphylaxis; or the therapeutic is contained within a tip of each of the microneedles in the array of microneedles, and the array of microneedles contains at least 1 μL of the therapeutic.

14. The method of claim 9, wherein the step of at least partially removing the microneedle patch from the hosing is carried out by a mechanical actuator.

15. The method of claim 9, wherein the delivering step delivers at least 1 μL of a therapeutic over a time of at least 10 minutes; the delivery rate is at least two times greater than the delivery rate of a passive microneedle patch without an acoustic signal; or the delivering step increases the concentration of therapeutic in the surface by at least 20 mg/mL when the delivery time is at least 6 minutes.

* * * * *